United States Patent
McGlothlin et al.

(10) Patent No.: US 7,374,711 B2
(45) Date of Patent: May 20, 2008

(54) ACCELERATOR-FREE THIN-WALLED RUBBER VULCANIZATES FROM LATEX

(75) Inventors: Mark W. McGlothlin, San Diego, CA (US); Eric Schmid, San Diego, CA (US); Brian P. Watschke, Eden Prairie, MN (US)

(73) Assignee: Apex Medical Technologies, Inc., San Diego, CA (US)

( * ) Notice: Subject to any disclaimer, the term of this patent is extended or adjusted under 35 U.S.C. 154(b) by 632 days.

(21) Appl. No.: 10/269,840

(22) Filed: Oct. 10, 2002

(65) Prior Publication Data

US 2004/0071909 A1    Apr. 15, 2004

(51) Int. Cl.
B29C 41/14    (2006.01)
B29C 35/00    (2006.01)

(52) U.S. Cl. .................. 264/301; 264/236; 264/306
(58) Field of Classification Search ............. 428/36.8; 264/301, 319, 344, 488, 306, 236
See application file for complete search history.

(56) References Cited

U.S. PATENT DOCUMENTS

| | | | |
|---|---|---|---|
| 3,179,718 A | 4/1965 | Wei et al. | |
| 3,215,649 A | 11/1965 | Preiss et al. | |
| 3,813,695 A | 6/1974 | Podell, Jr. et al. | |
| 3,937,862 A | 2/1976 | Dillenschneider | |
| 4,218,548 A | 8/1980 | Mageli et al. | |
| 4,695,609 A | 9/1987 | Stevenson | |
| 4,724,028 A | 2/1988 | Zabielski et al. | |
| 4,808,442 A | 2/1989 | Verlaan et al. | |
| 4,938,751 A | 7/1990 | Leeper et al. | |
| 4,973,627 A | 11/1990 | Mitchell | |
| 5,073,597 A | 12/1991 | Puydak et al. | |
| 5,254,635 A | 10/1993 | Stevenson et al. | |
| 5,504,168 A * | 4/1996 | Maestri et al. | ................. 526/83 |
| 6,051,320 A * | 4/2000 | Noecker et al. | ............. 428/447 |
| 6,075,073 A | 6/2000 | McGlothlin et al. | |
| 6,136,987 A * | 10/2000 | Fruh et al. | ................... 549/475 |
| 6,162,875 A | 12/2000 | Virdi | |
| 6,187,857 B1 * | 2/2001 | Ozawa et al. | ................ 524/565 |
| 6,245,861 B1 | 6/2001 | Class | |
| 6,300,421 B1 | 10/2001 | Blok et al. | |
| 6,329,444 B1 | 12/2001 | McGlothlin et al. | |
| 6,383,552 B1 * | 5/2002 | Noecker et al. | .............. 427/2.3 |
| 6,495,065 B1 * | 12/2002 | Lou et al. | .............. 252/183.12 |
| 6,569,375 B1 * | 5/2003 | McGlothlin et al. | ......... 264/488 |

FOREIGN PATENT DOCUMENTS

WO    WO 02/08328 A1    1/2002

* cited by examiner

Primary Examiner—Mathieu D. Vargot
(74) Attorney, Agent, or Firm—Townsend and Townsend and Crew LLP

(57) ABSTRACT

Thin-walled rubber articles for use contact with living tissue or with materials to be delivered to living tissue are prepared from aqueous latex of either natural rubber or synthetic cis-1,4-polyisoprene by vulcanization to produce both carbon-carbon and carbon-(sulfur)$_n$-carbon crosslinks, the vulcanization being performed in the absence of any compounding components that contain secondary amine groups or any components that have a tendency to produce nitrosamines. While sulfur activators may be included, it is preferable that no sulfur accelerators at all be included. Thin-walled rubber articles formed from the latex surprisingly exhibit a combination of high tensile strength, high ultimate percent elongation, and low 500% tensile modulus. The process is particularly effective in the manufacture of thin-walled articles from synthetic cis-1,4-polyisoprene.

34 Claims, No Drawings

ACCELERATOR-FREE THIN-WALLED RUBBER VULCANIZATES FROM LATEX

BACKGROUND OF THE INVENTION

1. Field of the Invention

This invention resides in the field of thin-walled rubber articles, and particularly those that are made from latex and vulcanized to produce both carbon-sulfur and carbon-carbon crosslinking bonds. The goal of this invention is to provide thin-walled rubber articles with favorable tensile characteristics including high tensile strength, high ultimate elongation, and low tensile modulus, and to do so without creating allergic reactions or health concerns that are attributable to some of the chemicals that are commonly used in the manufacture of sulfur-vulcanized rubber.

2. Description of the Prior Art

Natural and synthetic rubber have been used extensively as materials of construction for thin-walled medical devices and personal items. Examples of articles made from these materials are surgical and examination gloves, finger cots, catheter balloons and cuffs, uterine thermal ablation balloons, condoms, contraceptive diaphragms, in-dwelling urinary drainage catheters, male external urinary drainage catheters, breather bags, surgical tubing, baby pacifiers, baby bottle nipples, and drug infusion bladders. Because of the mechanical stresses imposed on these devices during use, the walls of these devices must have a high tensile strength combined with a low 500% tensile modulus. The rubber is vulcanized in any of various ways to achieve structural integrity, but high tensile strength and low tensile modulus are most readily achieved when vulcanization is achieved by the use of sulfur, i.e., by crosslinking of the polymer chains with carbon-sulfur bonds.

The highest durability and flexibility are achieved by a rubber film that is seamless and of uniform thickness. Thin-walled rubber devices formed from latex, particularly by dip-molding, are particularly favorable for these reasons. Latex can be processed without breaking down the molecular weight of the rubber, whereas dry-rubber methods, which utilize high shear to comminute the rubber and combine it with other compounding ingredients for processing, tend to degrade the molecular weight.

Vulcanization with sulfur has traditionally been performed in the presence of sulfur vulcanization accelerators. The first compound found to be capable of accelerating the reaction between sulfur and natural rubber was aniline (first used in 1906), and various other compounds bearing similarities to aniline were subsequently developed that were less toxic and produced greater acceleration activity. Included among these are:

mercaptobenzothiazoles, such as 2-mercaptobenzothiazole, bis(2,2'-mercaptobenzothiazolyl)disulfide, and zinc 2-mercaptobenzothiazole, sulfenamides, such as N-tert-butyl-2-benzothiazolesulfenamide, N-cyclohexyl-2-benzothiazolesulfenamide, N-oxydiethylene-2-benzothiazolesulfenamide, and 4-morpholino-2-benzothiazolesulfenamide, dithiocarbamates, such as bismuth dimethyldithiocarbamate, cadmium diethyldithiocarbamate, copper dimethyldithiocarbamate, zinc dimethyldithiocarbamate, and other metal dialkyldithiocarbamates, and piperidinium pentamethylenedithiocarbamate thiurams, such as dipentamethylene thiuram disulfide, dipentamethylene thiuram hexasulfide, tetramethylthiuram disulfide, tetrabenzylthiuram disulfide, and tetra-n-butylthiuram disulfide, guanidines, such as diphenylguanidine and di-ortho-tolylguanidine, thioureas, such as diphenylthiourea, ethylenethiourea, and trimethylthiourea, xanthates, such as dibutyl xanthogen disulfide and zinc di-iso-propylxanthate, and dithiophosphates, such as copper O,O-di-iso-propylphosphorodithioate and zinc O,O-di-n-butylphosphorodithioate The most widely used accelerators in the above list are those that contain secondary amine groups (RR'N—, as opposed to primary amine groups RNH—), such as dialkyl amino groups, cycloalkylamino groups, and morpholinyl groups. Secondary amine groups are found, for example, among the sulfenamides, the dithiocarbamates and the thiurams. An unfortunate consequence of the inclusion of these accelerators is their tendency to produce an adverse reaction in individuals with whom the articles come into contact. The reaction is commonly referred to as a Type IV allergy, which is mediated by T cells, generally occurs within six to 48 hours of contact with the rubber article, and is localized to the area of the skin where contact is made. Secondary amine-containing accelerators are also referred to as nitrosatable amines since they are susceptible to reaction with atmospheric nitrogen oxides during mixing, milling, extrusion, molding, calendaring, curing, and even warehousing and storage, to produce nitrosamines, which have been designated as potential human carcinogens. Some of these nitrosamines are N-nitroso-di-n-butylamine, N-nitrosodiethanolamine, N-nitrosodiethylamine, N-nitrosodimethylamine, N-nitrosodiisopropylamine, N-nitrosodi-n-propylamine, N-nitrosomorpholine, N-nitrosopiperidine, and N-nitrosopyrrolidine.

Natural rubber itself is responsible for adverse reactions in certain individuals, and these as well are addressed by certain embodiments of this invention. One type of adverse reaction to natural rubber is an indirect reaction that arises as a result of irritant dermatitis. Although not an allergic reaction, irritant dermatitis can cause breaks in the skin which can provide the components of the rubber, including proteins, increased access to the body's immune system and ultimately an allergic reaction. Another type of adverse reaction to natural rubber is a systemic allergic reaction known as a Type I allergy, which is caused by IgE antibodies to the proteins in natural rubber. This is an "immediate" reaction, occurring within thirty minutes of exposure, and its symptoms include hives, rhinitis, conjunctivitis, asthma, and in rare cases anaphylaxis and hypotension.

These adverse reactions to natural rubber can be prevented by using a suitable synthetic rubber. The use of deproteinized natural rubber has been proposed, but it has not been shown that deproteinized natural rubber eliminates the problems entirely. Various synthetic elastomers have been used as well. Nitrile rubber and polychloroprene, for example, have been used in the manufacture of surgical gloves, medical examination gloves, and dental gloves. These materials do not however offer the high resiliency and low tensile set values of natural rubber. Silicone rubber has been used for catheter balloons, but its tensile strength is lower than that of natural rubber and must be compensated for by an increased wall thickness. Polyurethanes have also been used, particularly in dip-molded catheter balloons. Polyurethanes have very high tensile strength, but they lack the resiliency and low tensile set values of natural rubber and are therefore unsuitable for devices that are required to undergo large degrees of expansion during use and then be able to return to their original configuration. Gloves have also been prepared from styrene-ethylene-butylene-styrene tri-block copolymer, but this material has very high tensile set values, a characteristic that causes the glove to exhibit undesirable "bagging," i.e., to remain stretched after use.

The closest substitutes for natural rubber in terms of overall performance are synthetic cis-1,4-polyisoprene and rubber compositions which are comprised of substantial amounts of synthetic cis-1,4 polyisoprene. There are considerable differences however between synthetic cis-1,4-polyisoprene and natural rubber in terms of molecular structure. The polyisoprene in natural rubber has a molecular weight of from about 1,000,000 amu to about 2,500,000 amu, while the molecular weight of synthetic cis-1,4-polyisoprene ranges from about 250,000 amu to about 350,000 amu (both expressed as number averages). Lower molecular weight polymers generally have lesser tensile properties, including lower tensile strength. Synthetic cis-1,4-polyisoprene also has a lower degree of branching, lower symmetry, and lower intermolecular forces. All of these characteristics contribute to and affect the tensile properties of the polymer.

Certain medical devices, such as surgical and other medical gloves, require a relatively low tensile modulus to remain comfortable during use. If the tensile modulus is too high, the user's hands may become fatigued over time as progressively more strength is required to stretch the glove material. This is particularly problematic with gloves that are to be used for a prolonged period of time such as during a long surgical procedure. The importance of a low tensile modulus is recognized in the standardized testing procedure ASTM D3577, which sets standards for the tensile properties. The standards require that the 500% modulus value be 7 MPa or less for synthetic gloves, and 5.5 MPa or less for natural rubber gloves. Low tensile modulus values are also important for condoms to promote ease of donning, and for catheter balloons where ease of inflation is beneficial. A low tensile modulus is also of value in elastomeric drug infusion bladders by making it easier to fill the bladder with a drug solution.

Another tensile property affecting the usefulness of certain medical and personal devices is tear strength, which is important in preventing premature failure of the device. Baby bottle nipples and baby pacifiers also benefit from high tear strength since this prevents the child's teeth from severing the nipple or pacifier during use. It is generally known that rubbers that are crosslinked only through carbon-carbon bonds have inferior tear strength compared to rubbers that contain sulfidic and/or polysulfidic crosslinks.

A still further tensile property that is important to the satisfactory performance of rubber medical devices is ultimate elongation. Increasing the ultimate elongation value is believed to reduce the incidence of breakage in use. This is of benefit for example to condoms and catheter balloons, as well as to surgical gloves which are easier to don if they have a high ultimate elongation value. The importance of high ultimate elongation is also recognized in the standard testing procedure ASTM D3577, which requires an ultimate elongation of at least 650% percent for synthetic gloves, and at least 750% for natural rubber gloves. In the case of catheter balloons, a high ultimate elongation lowers the stress that is placed on the balloon when inflated and thereby helps prevent premature failure. It is well known that for any given rubber composition, sulfur-vulcanized articles exhibit higher elongation than do equivalent articles which contain only carbon-carbon crosslinks.

The following is a survey of disclosures that may constitute prior art relevant to certain aspects of the invention set forth herein. The relevance of each of these disclosures will be apparent from the succeeding sections of this specification and claims. All patents and published materials cited throughout this specification are incorporated herein by reference in their entirety.

The use of cis-1,4-polyisoprene latex compositions for use in medical devices or medical device components is well known. Preiss et al. in U.S. Pat. No. 3,215,649, disclose the use of a sulfur-vulcanized cis-1,4-polyisoprene. McGlothlin et al. in U.S. Pat. No. 6,329,444 disclose the use of sulfur-free, free-radical-cured cis-1,4-polyisoprene for use in dip-molded medical devices. Leeper et al. in U.S. Pat. No. 4,938,751 disclose the use of reinforced free radical crosslinked cis-1,4-polyisoprene in elastomeric bladders. The Leeper et al. patent addresses molded (non-latex) rubber articles, but still of fairly thin walls. Both the McGlothlin et al. and Leeper et al. patents cite the high level dimensional stability of the cured polyisoprene materials, primarily due to the carbon-to-carbon crosslinking. McGlothlin et al. state that tensile set values of less than 5% can be achieved, while Leeper et al. reveal that a low frequency hysteresis less than about 10% and a stress relaxation less than about 10% can be achieved. Neither McGlothlin et al. nor Leeper et al. disclose the use of sulfur in combination with organic peroxides to improve the physical properties of synthetic polyisoprene.

Zabielski et al. in U.S. Pat. No. 4,724,028 disclose the use of a free radical curing mechanism to cure medical injection sites made from cis-1,4-polyisoprene via an extrusion process. Noecker et al. in U.S. Pat. No. 6,051,320 disclose the use of reinforcing agents to improve the tensile strength of free radical cured natural rubber for use in medical devices. Noecker et al. admit that ". . . the sample rubber latex gloves according to the invention are somewhat inferior in tensile strength and modulus of elasticity than the conventional rubber latex gloves formed using sulfur and related curing agents." The tensile strength cited by Noecker et al. for natural rubber is 21 to 24 MPa. There is no reference at all to synthetic polyisoprene. Neither the Zabielski et al. nor Noecker et al. patents provide any suggestion of combining sulfur and free-radical curing mechanisms to improve tensile strength.

Class in U.S. Pat. No. 6,245,861 states that compositions cured exclusively with peroxides are thought to have shorter crosslinks which are less flexible than comparable crosslinks from sulfur-cured compositions and therefore peroxide-cured compositions are believed to exhibit less resistance to abrasion and cut growth. While not directly referring to synthetic polyisoprene, Class addresses problems that generally arise with free-radical-cured rubber compounds.

The use of coagents has been suggested as a means to overcome the objections to pure peroxide cures. Typical coagents as disclosed by Class include trimethylolpropane trimethacrylate, triallyl isocyanate, pentaerythritol tetramethacrylate, trimethylolpropane trimethacrylate, triallyl isocyanate, pentaerythritol tetramethacrylate, and low molecular weight 1,2-polybutadiene. Class states that coagents can increase the modulus and hardness of a peroxide-cured composition. While suggesting the combination of both peroxide and sulfur in the same composition, Class does not suggest that sulfur is a coagent for the peroxide. Class specifically discloses however the use of traditional accelerators when sulfur is used. Class does not mention the use of polyisoprene, and does not mention medical device applications. In many medical device applications, the increase in hardness and modulus is not desirable, especially for thin-walled products such as condoms and gloves.

Blok et al. in U.S. Pat. No. 6,300,421 provide a comprehensive overview of the role of coagents in the curing of EPDM elastomers. Blok et al. further disclose the use of elemental sulfur as a coagent for peroxides in the curing of EPDM rubber. Also disclosed is the potential use of polyisoprene as a component of the EPDM formulation. Blok et al. further state that in order to minimize, or retard, the occurrence of side reactions, co-agent(s) may be used in combination with the peroxide curative to react with and stabilize the free radicals formed during the curing process. In this manner, a co-agent tends to improve the overall crosslinking efficiency and thereby lead to a higher cure rate and state of cure. This is well known to those having skill in such art. Blok et al. do not suggest that any carbon-sulfur bonds are actually formed. The sulfur is likely acting as a traditional coagent to help the efficiency, rate and state of cure, which will generally increase the tensile modulus and reduce the ultimate elongation of the rubber. Blok et al. do not disclose anything related to natural rubber or synthetic polyisoprene, or to medical devices or latex applications.

Magei et al. in U.S. Pat. No. 4,218,548 disclose the use of sulfur as a coagent for ethylene propylene rubber. As in Blok et al., there is no suggestion that the sulfur is acting as a vulcanizing agent. There is also no mention or suggestion by Blok et al. of the use of peroxide compounds with polyisoprene or for the curing of medical devices.

Sartomer Company, Inc., Exton, Pa., USA, manufactures a large number of products for use as peroxide coagents in curing elastomers. Sartomer has published a technical bulletin entitled "Coagent Selection for Peroxide Cured Elastomers." While not specific to synthetic polyisoprene, the bulletin contains references to co-agents for elastomers in general. Table 15 of the bulletin provides a generalized cure property comparison between a peroxide-only curing system, an accelerated sulfur-only curing system, and seven different peroxide-coagent curing systems. The data show that tensile modulus and hardness both increase with the addition of coagents, as compared to both accelerated sulfur-curing systems and to peroxide-only curing systems. This is not desirable from the perspective of making highly elastic medical devices such as condoms, gloves, balloons, and surgical tubing. The bulletin does not disclose the possibility of using sulfur in combination with peroxide.

An article by McElwee and Lohr entitled "Comparing curing systems: peroxide-coagent versus sulfur-accelerator in polyisoprene" appears in *Rubber World*, Kippincott & Peto, Inc, Akron, Ohio, USA, Volume 225, No. 2, November 2001, pages 41-44. The article states that a peroxide-coagent curing system has the best characteristics of both peroxide and sulfur cure systems, i.e., high tensile strength, high tear strength, high modulus, and outstanding flex and heat-aged properties. While several acrylic and other coagents are disclosed, the use of sulfur as a coagent is not disclosed. Comparisons are made between sulfur-cure, peroxide-cure, and peroxide/coagent cure in terms of several physical properties. The comparisons show that the tensile modulus obtained with the peroxide-coagent system is higher than that obtained with the other cure systems, indicating that the peroxide-coagent system achieves a greater state of cure. The Shore A hardness is also shown to be significantly higher with the peroxide-coagent system than for either the accelerated sulfur-cure or the peroxide-only cure, results that are consistent with other prior art observations. The article does not reveal the advantage of using sulfur in conjunction with peroxide to cure polyisoprene in terms of achieving a lower modulus and higher elongation without increasing the hardness of the material.

Stevenson in U.S. Pat. No. 4,695,609 A1 discloses a process for preparing a vulcanized rubber article using sulfur vulcanization with a combination of accelerators which include a dihydrocarbyl xanthogen polysulphide and less than 0.4 part by weight of nitrosatable materials. The accelerator combination is disclosed for use with synthetic polyisoprene. The process described in the patent reduces the amount of nitrosamine formation during curing, and achieves a significant reduction in the use of toxic conventional nitrogen-containing accelerators, but does not allow for the complete elimination of such compounds. The use of peroxide and sulfur in combination for vulcanization of polyisoprene is not disclosed.

Stevenson et al. in U.S. Pat. No. 5,254,635 disclose a means for reducing the amount of nitrosatable compounds needed in rubber formulations. While not specifically citing synthetic polyisoprene, Stevenson et al. state that the use of potentially nitrosatable materials such as secondary and tertiary amines may need to be added as supplemental accelerators to provide for a satisfactory degree of cure when the rubber to be cured is a synthetic rubber. Stevenson apparently was still able to limit the amount of these undesirable substances to about 0.2 phr. While this is a low level, its is still an undesirable amount for the fabrication of medical devices and components. Again, there is no disclosure of the use of peroxide and sulfur in combination for vulcanization of synthetic polyisoprene.

Virdi in U.S. Pat. No. 6,162,875 discloses the use of zinc diisononyldithiocarbamate as a sulfur accelerator which is thought to produce safer nitrosamines that are likely to be non-mutagenic. Vulcanizates produced by the Virdi process still contain nitrosamines, however.

Puydak et al. in U.S. Pat. No. 5,073,597 disclose the use of sulfur as a coagent for peroxide in curing EPM and EPDM rubbers for use in making dynamically vulcanized alloys that can be processed by thermoplastic forming methods. While the inclusion of synthetic polyisoprene in the composition is disclosed, the role of the polyisoprene is not defined and no mention is made of vulcanization of the optional polyisoprene. No special characteristics are assigned to the peroxide-cured compositions that use sulfur as a coagent. Furthermore, the use of dynamic vulcanized rubber materials is limited and cannot be used to produce high tensile strength, low tensile set rubber materials.

Numerous methods for the vulcanization of peroxide-containing formulations are known. Most of these methods involve excluding oxygen from the rubber composition during the curing process. McGlothlin et al. in U.S. Pat. No. 6,329,444 disclose methods to protect thin films of organic peroxide-containing polyisoprene from oxygen exposure during vulcanization. Verlaan et al. in U.S. Pat. No. 4,808,442 teach several methods to protect organic peroxide-containing rubber compositions from degradation caused by oxygen attack of the rubber. Compression, transfer and injection molding are known methods of protecting such rubber compositions during the curing process.

Organic peroxide-cured rubber particles can be prevulcanized prior to being formed into shaped articles if oxygen is mostly excluded during the prevulcanization process. One such process, in which dicumyl peroxide is used to prevulcanize synthetic latex rubber particles is disclosed by Bayer AG (Obrecht) in WO 02/08328 A1.

Dillenschneider in U.S. Pat. No. 3,937,862 discloses tire sidewalls formed from a mixed sulfur and peroxide vulcanization system (Example 23) with an EPDM polymer having a relatively low molecular weight (Mooney viscosity of 84 at 100° C.). Dillenschneider concludes that the mixed vulcanization system offers no particular advantage over an all-peroxide vulcanization system. While Dillenschneider discloses the use of mixtures of rubbers, some of which may include polyisoprene and/or natural rubber, the patent does not disclose the use of a mixed sulfur and peroxide vulcanization system for polyisoprene-containing blends. All of the disclosed compositions include the use of nitrosatable rubber accelerators. Dillenschneider further states that the use of sulfur in very small amounts, such as from about 0.1 to about 0.3 phr, would be insufficient for vulcanization in the absence of both peroxide and an accelerator.

Wei et al. in U.S. Pat. No. 3,179,718 teach the use of a mixture of peroxide and elemental sulfur to vulcanize blends of highly saturated rubber with butadiene-acrylonitrile rubber. In comparative examples, Wei et al. refer to the curing of natural rubber with a combination of sulfur and peroxide. The form of natural rubber used by Wei et al. was smoked sheet rubber. When compounding natural rubber with a combination of 2 phr of sulfur and 4 phr of dicumyl peroxide, Wei et al. produced a vulcanizate with a tensile strength of 2360 psi and an ultimate elongation of 570%. While Wei et al. suggest that synthetic polyisoprene can be blended with other rubber material and then vulcanized with a sulfur/peroxide curing system, there is no mention of the use of synthetic polyisoprene alone. Nor do Wei et al. disclose the use of latex formulations, or state that the disclosed curing system produces a product with high tensile strength. Nor do Wei et al. mention avoidance of Type I or Type IV latex allergies. Still further, the only rubber articles that Wei et al. address are tire treads, windshield channels, and cable coverings. Thin-film rubber articles are not addressed or suggested.

Mitchell in U.S. Pat. No. 4,973,627 teaches the use of a tire sidewall composition that includes a mixed sulfur and peroxide vulcanization system. The optional inclusion of polyisoprene and/or natural rubber in the sidewall composition is mentioned. The patent expressly states that it is necessary to include sulfur accelerators in the manufacture of the disclosed product.

Podell, Jr., et al. in U.S. Pat. No. 3,813,695 disclose the application of acrylic hydrogel coatings to gloves to serve as donning aids. No disclosure is made of such coatings being used to eliminate the passage of oxygen during the peroxide curing of gloves.

The prior art indicates that thin-walled latex dip-molded rubber articles with a combination of excellent tensile strength, low 500% modulus, and high ultimate elongation, can only be obtained by vulcanization with sulfur in combination with a nitrosatable (i.e., secondary amine-containing) sulfur accelerator. The present invention overcomes this limitation.

SUMMARY OF THE INVENTION

It has now been discovered that thin-walled rubber articles can be formed that exhibit highly favorable tensile properties and yet contain no components that produce either nitrosamine formation or Type IV allergic reactions. These articles are formed by vulcanizing an aqueous latex to form both carbon-sulfur and carbon-carbon crosslinks without the inclusion in the latex of any reactive species that contain secondary amine groups. The most commonly used secondary amine-containing reactive species in the prior art are sulfur vulcanization accelerators. Certain agents that contain both sulfur and secondary amine groups serve as either sulfur vulcanizing agents themselves or as both sulfur vulcanizing agents and sulfur accelerators, and these are excluded in this invention as well. Examples of these agents are 4,4'-dithiodimorpholine, 2-(4-morpholinyldithio)benzothiazole, tetramethylthiuram disulfide, tetraethylthiuram disulfide, dipentamethylenethiuram hexasulfide, and N,N'-caprolactam disulfide. In preferred embodiments of this invention, the latex contains no sulfur accelerators at all nor any other reactive species that contain secondary amine groups. The term "reactive species" is used herein to refer to species that are not inert during the vulcanization stages or any of the processing steps, and the term "secondary amine group" is used in accordance with the definition given above. The carbon-sulfur crosslinks are formed by sulfur-containing vulcanizing agents, elemental sulfur itself being preferred, and the carbon-carbon crosslinks are formed by any vulcanizing method that forms carbon-carbon bonds, peroxides being the preferred vulcanization agent. The favorable tensile properties include a high ultimate percent elongation, a low tensile modulus (for example a low 500% tensile modulus), a high tear strength, and a high tensile strength. Further advantages are obtained by using synthetic cis-1,4-polyisoprene as the rubber component, but the invention as a whole extends to both synthetic cis-1,4-polyisoprene and natural rubber.

Thin-walled rubber articles in accordance with this invention are primarily contemplated for direct or indirect contact with living tissue, as well as for direct contact with liquids intended for infusion into human patients and for contact with gases intended for inhalation. Examples of these articles are medical gloves, condoms, diaphragms, catheter balloons, drug infusion bladders, tissue retrieval pouches, medical tubing, baby bottle nipples, infant pacifiers, anesthesia bags, resuscitation bags, and surgical tubing. Other examples will be apparent to those skilled in medical procedures and the various types of equipment used in these procedures.

DETAILED DESCRIPTION OF THE INVENTION

While not intending to be bound by theory, the inventors herein believe that crosslinks formed in the practice of this invention include carbon-to-carbon crosslinks, monosulfidic carbon crosslinks (C—S—C), and polysulfidic carbon crosslinks (C—$S_n$—C), the monosulfidic and polysulfidic carbon crosslinks being referred to herein collectively as "carbon-sulfur crosslinks."

Carbon-sulfur crosslinks in accordance with this invention are obtained by conventional means involving the use of sulfur-containing vulcanization agents, of which various examples are well known in the art. The most common agent is elemental sulfur itself, most often used in the rhombic polymerized form as a cyclic eight-membered ring. Sulfur-donating compounds that cannot form nitrosamines are known in the art and can be used as well, although elemental sulfur is preferred. For processes involving elemental sulfur, the amount of sulfur included in the latex can vary, but preferred amounts are 10 phr or less, more preferably from about 0.01 phr to about 6 phr, and most preferably from about 0.1 phr to about 0.6 phr. The term "phr" means "parts hundred ratio," or parts by weight per hundred parts by weight of dry rubber. As noted above, sulfur-containing vulcanization agents that produce nitrosamines are not used in the practice of this invention.

Carbon-carbon crosslinks in accordance with this invention are obtained by conventional means as well, notably by the use of free-radical vulcanizing agents. Preferred among these are organic peroxides, of which the most common are diacyl peroxides, dialkyl peroxides, peroxyketals, monoperoxycarbonates, acetyl alkysulfonyl peroxides, dialkyl peroxydicarbonates, tert-alkyl hydroperoxides, peroxyesters, and acetylalkyl-sulfonylperoxides. Two particularly preferred peroxides are dicumyl peroxide, available from Hercules Incorporated, Wilmington, Del., USA, as DiCup R, and di-(2-tert-butyl peroxy isopropyl) benzene, available from R. T. Vanderbilt Company, Inc., Norwalk, Conn., USA, as VAROX® VC-R. Examples of other useful dialkyl peroxides are 2,5-dimethyl-di-(t-butylperoxy)hexane, dibenzoyl peroxide, di-t-butylperoxide, t-butylcumyl-peroxide, bis(t-butylperoxyisopropyl)benzene, n-butyl 4,4-bis(t-butylperoxy)valerate, 2,5-bis(t-butylperoxy)-2,5-dimethylhexane, 2,5-bis(t-butylperoxy)-2,5-dimethyl-3-hexyne, t-butyl 3-isopropylcumyl peroxide, bis(3-isopropenylcumyl) peroxide, 1,1-bis(t-butylperoxy)-3,3,5-trimethylcyclohexane, t-butylperoxybenzoate, and bis(2,4-dichlorobenzoyl) peroxide. Still others are known to those skilled in the art. The amount of peroxide can vary, and using dicumyl peroxide as an illustration, preferred amounts are in the range of from about 0.05 phr to about 3 phr, preferably from about 0.1 phr to about 2 phr, and most preferably about 1.2 phr.

Alternatives to peroxides are difunctional crosslinking agents such as hydroxyl compounds and diamino compounds. Examples of hydroxy compounds are p-quinone dioxime, methylolphenol-formaldehyde resin, and alkylphenol-formaldehyde resin. Examples of diamino compounds are hexamethylenediamine carbamate, N,N'-dicinnamylidene-1,6-hexanediamine, 4,4'-methylenebis(cyclohexylamine)carbamate, and 4,4'-methylenedianiline. Further vulcanizing agents are disclosed in U.S. Pat. No. 3,892,697, issued Jul. 1, 1975, to O. W. Burke.

Coagents, activators, and other additives that are known in the art of rubber manufacturing can be included in the latices used in the practice of this invention. Zinc oxide, for example, is useful as a sulfur activator, and is preferably included in an amount ranging from about 0.03 phr to about 1 phr. Further examples are coagents for peroxide systems. Certain coagents add to the crosslinking efficiency of the peroxides by causing a single peroxide radical to produce more than one carbon-carbon crosslink. Coagents can also be integrated into the polymer network by covalent bonds to enhance certain properties of the polymer, such as elongation and tear strength. Some of these coagents are based on acrylate and methacrylate chemistry. Examples are SARET® 231, SARET 516, SARET 517, SARET 521, and SARET 634, available from Sartomer Company, Inc., Exton, Pa., USA. These coagents are multifunctional salts of acrylic and methacrylic acids. Of these, SARET 634 (whose primary ingredient is zinc dimethacrylate) and SARET 231 and 521 (whose primary ingredients are difunctional acrylate esters, SARET 521 further containing a scorch retarder) are the most preferred. Trimethylolpropane trimethacrylate, triallyl isocyanate, pentaerythritol tetramethacrylate, low molecular weight 1,2-polybutadiene, and polychloroprene are further examples. More extensive lists of coagents are found in U.S. Pat. No. 3,751,878, issued Aug. 7, 1973 to Cowperthwaite et al., and U.S. Pat. No. 5,310,811, issued May 10, 1994 to Cottman et al.

Reinforcing agents and other additives are also included in some embodiments of the invention. Examples of reinforcing agents are silica (notably fumed silica), carbon black, and chopped fibers. The use of fibers to improve the tear strength of medical gloves is disclosed in U.S. Pat. No. 6,021,524, issued Feb. 8, 2000, to Wu et al., and the use of fumed silica to improve the tear strength of dipped films is disclosed in U.S. Pat. No. 5,872,173, issued Feb. 16, 1999, to Anand. Antioxidants and antiozonants may also be included to protect against environmental aging. Preferred antioxidants are hindered phenolic compounds, examples of which are 4-{[4,6-bis(octylthio)-s-triazin-2-yl]amino}-2,6-di-t-butylhphenol, 2,4-bis[(octylthio)methyl]-o-cresol, and polymerized 1,2-dihydro-2,2,4-trimethylquinoline. Small amounts of other rubber materials can also be included as additives or blending agents. The use of carboxylated styrene butadiene rubber with at least 50% styrene content is preferred. This material appears to act as a reactive reinforcing agent, and possibly also serves as a peroxide coagent, imparting extra tensile strength. Pigments and dyes may also be included, as may any of the other additives known to those skilled in the art of rubber formulations and the manufacture of rubber devices.

The aqueous lattices used in the practice of this invention are aqueous lattices of either natural rubber or synthetic cis-1,4-polyisoprene. Natural rubber can be obtained from several sources, including *Hevea brasiliensis*, *Parthenum argentatum* (commonly known as "guayule"), and *Ficus elastica* rubber trees. Methods for obtaining natural rubber latices from non-Hevea sources are described in U.S. Pat. No. 5,580,942, issued Dec. 3, 1996, to Cornish. Natural rubber latex is available in several grades, including high ammonia latex, low ammonia latex, and others. All such varieties are suitable for use in the present invention. This invention also extends to natural rubber latices that have been processed to reduce the amount of proteins present in the latices. Some of these processes include centrifuging to separate and remove water, and others include double centrifuging, in which an initial centrifuging is followed by the addition of water and a second centrifuging. Still other processes involve the use of enzymes to digest the proteins. Descriptions of enzyme methods are found in U.S. Pat. No. 5,610,212 Mar. 11, 1997, U.S. Pat. No. 5,569,740, Oct. 29, 1996, and U.S. Pat. No. 5,585,459, Dec. 17, 1996, to all Tanaka et al. An example of a commercially available deproteinized rubber latex is ALLOTEX®, obtainable from Tillotson Healthcare Corporation, Rochester, N.H., USA.

Synthetic cis-1,4-polyisoprene is commercially available in the United States from The Goodyear Tire & Rubber Company, Beaumont, Tex., USA., in Western Europe from Kraton Polymers Division of Ripplewood Holdings LLC, Bemis, Netherlands, and in Japan from Japan Synthetic Rubber Co., Ltd., and from Nippon Co., Ltd. The polymer is produced by polymerizing isoprene over a Ziegler catalyst consisting of isobutylaluminum and titanium tetrachloride, or alkali metal catalysts such as finely divided lithium metal or organolithium compounds. Other catalysts known in the polyisoprene art can be used as well. The polymer is also capable of preparation by processes involving anionic polymerization, cationic polymerization, and free-radical polymerization. These processes, and the conditions under which they are performed are known in the art. For typical synthetic cis-1,4-polyisoprene prior to crosslinking, the weight-average molecular weight generally ranges from about 750,000 amu to about 950,000 amu, and the number-average molecular weight generally ranges from about 250,000 amu to about 350,000 amu. Synthetic cis-1,4 polyisoprene prepared by the Ziegler catalyst route has about 96 to about 98% of its monomeric units joined in cis-1,4 orientation. In those made via anionic polymerization, about 90% to about 92% of the monomeric units are joined in cis-1,4 orientation. Preferred synthetic cis-1,4-polyisoprenes for use in this invention are those produced either by the Ziegler catalyst method or by anionic polymerization methods.

Latices of cis-1,4-polyisoprene are formed by methods known to those skilled in the art of rubber compounding and processing. These methods include either emulsification of an organic solution of the polymer in an aqueous medium followed by removing the solvent, or liquefaction of the polymer and combining the liquefied polymer with the aqueous medium under emulsification conditions. The emulsion can be stabilized by various emulsifying agents. Typical emulsifying agents are potassium and sodium salts of rosin acids and higher fatty acids, such as potassium and sodium salts of oleic acid, palmitic acid, stearic acid, lauric acid, myristic acid, arachidic acid, and ricinic acid, as well as sulfates and sulfonates of these acids, such as sodium lauryl sulfate and sodium lauryl sulfonate. Other emulsifying agents are amine salts of hydroxylamines of long-chain fatty acid esters, quaternary ammonium salts such as stearyldimethylbenzylammonium chloride and tridecylbenzenehydroxyethylimidazole chloride, phosphoric esters of higher alcohols such as capryl and octyl alcohol, and monoesters of oleic acid and pentaerythritol such as sorbitan monooleates. The relative amounts of each phase may vary, although in most cases, the volume ratio (organic:aqueous) will range from about 0.5:1 to about 20:1, and preferably from about 0.75:1 to about 1.25:1, for best results. When an organic solvent is used, suitable solvents are aliphatic hydrocarbons, preferably those containing 5 to 8 carbon atoms, examples of which are pentane, pentene, hexane, heptane, cyclohexane, cyclopentane, and tetrahydrofuran. The solvent is readily removed by evaporation of other conventional means to leave the solvent-free aqueous latex. If desired, the latex can then be concentrated by conventional methods, one example of which is ultrafiltration as disclosed by DelPico, U.S. Pat. No. 4,160,726 (Jul. 10, 1979) and by Tanaka et al., U.S. Pat. No. 5,569,740 (Oct. 29, 1996).

The various components of the latex can be combined in any manner that will produce a fluid medium with uniformly dispersed solids or droplets. Preferably, the individual components are first rendered in fluid form, either as solutions or aqueous-based emulsions or dispersions. The individual fluids are then combined by simple mixing to form the latex.

Vulcanization in the practice of this invention can be performed either (i) on the latex prior to thin film formation (in which case, the vulcanization is referred to as "prevulcanization"), (ii) after the thin film has been formed and dried ("postvulcanization"), (iii) after the thin film has been formed but before the water removed, or both before the thin film is formed and after the film has been formed and dried. Thus, prevulcanization can be either a partial or a complete vulcanization, and partial prevulcanization can be followed by completion of the vulcanization after the film is formed, or formed and dried. Prevulcanization can be achieved by heating the latex or applying high-energy radiation, optionally in the presence of vulcanization catalysts known in the art. The temperature and exposure time for heating are readily selected on the basis of the desired degree of prevulcanization. For high-energy radiation, a description is found in McGlothlin et al., U.S. Pat. No. 6,329,444, Dec. 11, 2001.

Formation of the latex into a thin film can be accomplished by any conventional method, including spraying, rolling, the use of a doctor blade, or various molding techniques well known in the art. For many medical and personal devices, particularly those that are hollow, such as condoms, surgical and examination gloves, and finger cots, dip molding is an especially effective and convenient means of forming the thin film. Dip molding involves the use of a forming member (or dip former) whose outer contour is complementary to that of the final article. The forming member is dipped in the latex, then removed at a controlled rate to leave a thin film of wet latex on the surface of the forming member. Two or more dips may be performed in succession, with partial drying between dips, to form the film in multiple layers if the desired thickness is not achieved with a single dip. The latex is subjected to vulcanization conditions either before or after dipping, and water is ultimately removed from the resulting film to leave the finished article.

Although the final film thickness is not critical to this invention, preferred films are those whose thickness is about 0.02 inch (0.051 cm) or less, most preferably from about 0.001 inch (0.0025 cm) to about 0.02 inch (0.051 cm). For surgical gloves, a particularly preferred thickness range is from about 0.003 inch to about 0.015 inch (about 0.0076 cm to about 0.038 cm). For condoms, a particularly preferred thickness range is from about 0.002 inch to about 0.005 inch (about 0.005 cm to about 0.013 cm). Other devices, such as catheter balloons, may have different ranges that are particularly preferred, but all will be within the broader ranges cited above, and all will be readily apparent to those skilled in the manufacture of such devices.

When the film is formed by dip molding, improved film qualities can be achieved by dipping the forming member in a liquid coagulant solution prior to the latex. Coagulants used in the rubber industry can be used here. Typical coagulants are polyvalent metal salts, examples of which are calcium nitrate and mixtures of calcium nitrate and calcium chloride.

When vulcanization is performed on the film, any of various known vulcanization methods can be used. Included among these are the use of a hot air curing oven, irradiation of the film with high energy radiation, and immersion of the film in a hot liquid media bath.

High energy radiation can be applied by electron beam radiation, for example at a power of from about 200 KeV to about 3 MeV and a current of about 25 Ma to about 200 Ma, or by gamma radiation, for example using either $^{60}$Co, $^{137}$Cs, $^{210}$Po, or $^{226}$Ra as the radiation source. Both electron beam radiation and gamma radiation can be enhanced by the inclusion of a chemical sensitizer in the latex. The peroxide compounds described above can serve as sensitizers. Other sensitizers are 1,3-butylene glycol diacrylate, 1,3-butylene glycol dimethacrylate, 1,6-hexanediol diacrylate, neopentyl glycol diacrylate, neopentyl glycol dimethacrylate, ethyl acrylate, n-butyl acrylate, n-hexyl acrylate, and 2-ethylhexylacrylate. The radiation dosage can vary. When no sensitizer is present, a typical dosage range is from about 20 megarads to about 40 megarads, and preferably about 25 megarads. When a sensitizer is used, a preferred dosage range for gamma radiation is from about 1 megarad to about 5 megarads, and a preferred dosage range for electron beam radiation is from about 10 megarads to about 20 megarads.

A preferred method of vulcanization is the immersion of the film in a liquid media bath, commonly referred to as the liquid curing method (LCM vulcanization). Although commonly applied to extruded rubber, a description of this method as applied to latex films is found in International Patent Application Publication No. WO 01/77210, Apex Medical Technologies, Inc., publication date Oct. 18, 2001, and its United States counterpart, pending patent application Ser. No. 09/547,366, filed Apr. 11, 2000. Liquid media that can be used for this purpose include molten inorganic salts, oils, glycols, liquefied metals, water, and brine solutions. Molten inorganic salts, silicone oils, and glycols are preferred, and molten inorganic salts are the most preferred. Examples of suitable molten inorganic salts are nitrates, nitrites, carbonates, sulfates, phosphates, and halides of potassium, sodium and lithium, as well as combinations of these salts. Salt combinations of this type are commercially available from such suppliers as Heatbath Corporation, Detroit, Mich., USA, and Hubbard-Hall Inc., Inman, S.C., USA. An example of a suitable commercial salt mixture is QUICK CURE 275 of Hubbard-Hall, Inc., the main components of which are potassium nitrate (approximately 50% by weight), sodium nitrite (approximately 30% by weight), and sodium nitrate (less than 10% by weight), with a molten temperature range of about 315° F. to 650° F. (157° C. to 343° C.). Other examples are PARCURE 275 and PARCURE 300 of Heatbath Corporation.

When a liquid media bath is used, the optimal temperature and the exposure time of the latex to the bath may vary with the latex composition. For natural rubber latex, for example, it is best not to exceed 450° F. (232° C.), while for synthetic cis-1,4-polyisoprene, slightly higher temperatures can be used. In general, a preferred temperature range is about 100° C. to about 350° C. The exposure time for organic peroxide curing systems, for example, is preferably long enough to ensure that virtually all of the organic peroxide in the system is homolytically cleaved, although excess peroxide can be leached out by solvent or water extraction. A minimum of six half-lives of the peroxide compound is preferred, and eight or more half-lives is most preferred.

Vulcanization of the thin film is preferably performed without contacting the film with molecular oxygen. This is readily accomplished by the use of an oxygen-excluding liquid media bath, but can also be accomplished by the use of closed molds, oxygen-free atmospheres, oxygen-scavenging chemicals, and barrier coatings. Other methods will be apparent to those skilled in the art. Barrier coatings can be applied by dipping the film, still on the forming member, in a solution of a barrier material, or by applying a barrier coating by other conventional means such as spraying or brush coating. Materials that serve effectively as barrier coatings are polyvinyl alcohol and acrylic and methacrylic coatings of the regular and hydrogel type. Once protected by the coating, the film can be vulcanized in a traditional hot air curing oven.

The following is one example of a procedure for dip molding and curing that can be used in the practice of this invention:

(a) Either a natural rubber latex or a synthetic rubber latex is compounded with vulcanizing agents and possibly additives such as a reinforcing agent, a stabilizer, a pigment, or two or more such additives.

(b) The compounded latex may then be partially or fully prevulcanized by heat or radiation.

(c) A forming member is optionally coated with a chemical coagulant by dipping the member into a bath containing the coagulant, then withdrawing the member and drying the coagulant film that is left on the surface of the member.

(d) The forming member, with or without the coagulant coating, is dipped in a bath of the compounded latex.

(e) The forming member is slowly withdrawn from the bath. If a coagulant coating was first applied, the surface of the forming member will be covered with a wet latex gel. If no coagulant coating was applied, the surface will be covered with a liquid latex film.

(f) Excess water in the latex gel or film on the forming member surface is removed, generally by evaporation in a hot air convection oven with either sweep gas or a partial vacuum. The hot air treatment can be supplemented with infrared, microwave, or radiofrequency radiation, or other types of energy to expedite the evaporation. If drying is performed under vacuum, there will be no need to apply heated air to the latex prior to the final vulcanization.

(g) The forming member is immersed in a heated liquid media bath for sufficient time to cure the latex.

(h) The forming member with the cured latex film is withdrawn from the heated media bath and cooled either in air or in a stream of water. Water may be used to rinse off any solidified salt that may have deposited from the media bath.

(i) The finished vulcanized latex article is manually or mechanically stripped from the forming member.

The following examples are offered for purposes of illustration and are not intended to set limits on the scope of the invention.

EXAMPLE 1

This example illustrates the use of combined sulfur and peroxide curing systems and the absence of a sulfur accelerator on an aqueous latex of synthetic cis-1,4-polyisoprene.

Materials

A synthetic cis-1,4-polyisoprene latex containing approximately 60% solids, Product No. IR-RP401 of Kraton Polymers, was used.

A master batch of 40% solids dicumyl peroxide dispersion was prepared by mixing the following materials for two minutes under high shear: 100 g of dicumyl peroxide, 35 g of toluene, 5.6 g of oleic acid, 101 g of deionized water, and 2.6 g of 30 weight percent aqueous potassium hydroxide solution. This resulted in a dispersion in which the dicumyl peroxide was uniformly dispersed.

A master batch of SARET 231 (a difunctional methacrylate coagent for the dicumyl peroxide) dispersion was prepared by mixing 5.6 grams of oleic acid with 35 grams of toluene for two minutes under high shear, then completely dissolving 100 g of SARET 521 in the resulting mixture. This was then added to 101 g of deionized water and 2.62 g of 30 weight percent aqueous potassium hydroxide solution. These materials were then mixed for 2 minutes under high shear. This produced a uniform dispersion.

A water-dispersed fumed silica was also utilized as a reinforcing agent. The silica was a 15% (by weight) aqueous dispersion (CABO GUARD LT-122) supplied by Cabot Corporation, Boston, Mass., USA.

The sulfur was a 68% active sulfur dispersion bearing the product name Bostex 410, supplied by Akron Dispersions, Akron, Ohio, USA. A zinc oxide dispersion was also used, consisting of 62% active zinc oxide bearing the product name Octocure 462, supplied by Tiarco Division of Textile Rubber and Chemical Co., Inc., Dalton, Ga., USA.

Additional components included were 5 phr of a high styrene content carboxylated SBR rubber latex (TYLAC 68333-00-20 from Reichhold Chemicals, Research Triangle Park, N.C., USA) as a reinforcing agent, 0.5 phr of surfactant, and 2 phr of the antioxidant 4-{[4,6-bis(octylthio)-s-triazin-2-yl]amino}-2,6-di-t-butylphenol All materials were mixed together under very low shear conditions and diluted to 45% total solids content with deionized water prior to use. Two compositions were prepared, differing only in the amount of sulfur, and each one including 0.2 phr of zinc oxide and 1 phr of fumed silica.

A coagulant solution was prepared by combining approximately 200 g calcium nitrate, 5 g Igepal CO-630 surfactant (supplied by Rodia, Inc., Cranbury, N.J., USA), and 795 g denatured ethyl alcohol.

Preparation of Test Films

A cylindrical glass former was dipped into the coagulant solution, allowed to dwell for five seconds, then withdrawn and allowed to air dry. The former was then immersed into compounded latex for a period of five seconds, then slowly withdrawn. The former was then dried in a hot air oven at 60° C. for sixty minutes. Once dried, the former and its adherent film were immersed in a molten salt bath for nine minutes at 177° C. The resultant film was then removed from the salt bath, rinsed, stripped and readied for tensile testing. Three films were prepared in this manner for each formulation to obtain three separate test specimens for tensile testing.

Determination of Tensile Properties

Standard condom ring tensile specimens were prepared and tested in accordance with ASTM specification D3492. The median tensile values from each series of three tests are listed in Table I.

TABLE I

Tensile Properties of Synthetic Polyisoprene Films Cured With
Both Sulfur and Peroxide But Without Sulfur Accelerators

| Test No. | Weight Ratio of Dicumyl Peroxide to SARET 231 | PHR of Combined Peroxide and SARET | PHR of Sulfur | 100% Modulus (PSI) | 300% Modulus (PSI) | 500% Modulus (PSI) | Ultimate Tensile Strength (PSI) | Ultimate Elongation (%) |
|---|---|---|---|---|---|---|---|---|
| 1.1 | 35/65 | 2.75 | 0.2 | 79 | 157 | 279 | 3329 | 950 |
| 1.2 | 35/65 | 2.75 | 0.4 | 86 | 161 | 270 | 3732 | 1005 |

The modulus values in Table I are favorably low and the tensile strengths and ultimate elongations favorably high.

EXAMPLE 2

This example further explores the sulfur and peroxide curing systems, both alone and in combination as well as in varying amounts, without using either a sulfur accelerator or a peroxide coagent, on an aqueous latex of synthetic cis-1,4-polyisoprene. The purpose was to investigate the effect of these variations on the improvements in tensile properties observed in Example 1.

The procedures for preparing the materials were the same as those of Example 1, and the tensile testing procedure utilized was ASTM D412, which is commonly used in the tensile testing of surgical gloves but yields results that are comparable to those obtained with ASTM D3492 used in Example 1. A toluene swell test was also conducted to partially quantify the degree of crosslinking. A decrease in the percentage swelling correlates with an increase in crosslink density. Carbon-carbon crosslinks tend to lower the toluene swelling more than do carbon-sulfur (C—$(S)_n$—C) crosslinks, since the carbon-carbon bonds are shorter and thereby hold the polymer chains more closely together. Thus, while the toluene swell value does not provide an exact correlation with crosslink density due to the different types of crosslinks, the toluene swell value is nevertheless useful as a means of comparing crosslink densities.

The toluene swell value was measured as a percent and was obtained by cutting three disks from each rubber sheet to be tested, using a 0.25-inch (0.635-cm) diameter round steel die. The disks were placed in a small glass jar filled with 10 mL of toluene where they were allowed to swell for thirty minutes. The disks were then removed and their diameters immediately measured. The percent swell was calculated as follows:

$$\% \text{ Swell} = \frac{(\text{Swollen Diameter}) - (\text{Initial Diameter})}{(\text{Initial Diameter})} \times 100$$

The tensile properties and percent toluene swells for various rubber compositions are listed in Table II below.

TABLE II

Tensile Properties of Synthetic Polyisoprene Films With
Varying Levels of Sulfur and Peroxide and No Accelerators
or Coagents

| Test Number | PHR Dicumyl Peroxide | PHR of Sulfur | 500% Modulus PSI | Ultimate Tensile Strength PSI | Ultimate Elongation - Percent | Toluene Percent Swell |
|---|---|---|---|---|---|---|
| 2.1 | 0 | 0.4 | 59 | 319 | 1885 | 206 |
| 2.2 | 0 | 1 | 77 | 490 | 1560 | 160 |
| 2.3 | 0 | 2 | 109 | 1121 | 1460 | 124 |
| 2.4 | 0.2 | 0.8 | 141 | 1781 | 1376 | 112 |
| 2.5 | 0.2 | 1 | 138 | 1558 | 1380 | 113 |
| 2.6 | 0.2 | 2 | 161 | 1558 | 1312 | 115 |
| 2.7 | 0.6 | 0.6 | 196 | 3368 | 1312 | 97 |
| 2.8 | 0.6 | 0.8 | 170 | 2861 | 1340 | 97 |
| 2.9 | 0.6 | 1 | 207 | 3196 | 1284 | 95 |
| 2.10 | 1.1 | 0 | 333 | 3286 | 944 | 90 |
| 2.11 | 1.1 | 0.4 | 280 | 3731 | 1128 | 88 |
| 2.12 | 1.1 | 0.6 | 206 | 3268 | 1256 | 89 |
| 2.13 | 1.1 | 0.8 | 239 | 3734 | 1204 | 91 |
| 2.14 | 1.2 | 0 | 405 | 3432 | 856 | 85 |
| 2.15 | 1.2 | 0.2 | 294 | 3437 | 1028 | 88 |
| 2.16 | 1.2 | 0.4 | 194 | 3160 | 1260 | 93 |
| 2.17 | 1.2 | 0.6 | 202 | 3441 | 1308 | 96 |
| 2.18 | 1.3 | 0 | 336 | 3229 | 936 | 86 |
| 2.19 | 1.3 | 0.2 | 310 | 3644 | 1032 | 89 |
| 2.20 | 1.3 | 0.4 | 289 | 4247 | 1080 | 83 |
| 2.21 | 1.3 | 0.6 | 215 | 3127 | 1248 | 92 |
| 2.22 | 1.3 | 0.8 | 206 | 3900 | 1132 | 87 |
| 2.23 | 1.5 | 0.2 | 268 | 3347 | 1032 | 79 |
| 2.24 | 1.5 | 0.4 | 350 | 4065 | 972 | 78 |

Comparison of the three test compositions in which no sulfur was present (Test Nos. 2.10, 214, and 2.18) with the remaining test compositions demonstrates that the addition of any amount of sulfur results in increased ultimate elongation and a reduction in the 500% tensile modulus. The comparison also shows that in an overwhelming number of test compositions, vulcanization with sulfur produced an increase in the tensile strength. It will also be noted from the succeeding examples that with peroxide vulcanization alone, even with a coagent, it is not possible to maintain tensile strength while reducing the 500% tensile modulus.

EXAMPLE 3

This example illustrates the process of the invention as applied to natural rubber latex.

The compounding materials consisted of low ammonia natural rubber with sulfur and dicumyl peroxide in amounts listed in Table III below, plus 2 phr fumed silica and 0.5 phr of the surfactant and 2 phr of the antioxidant used in Example 1. Zinc oxide was not included, nor was SBR rubber in view of the reinforcing structure that is inherent in natural rubber. The same testing procedures were used, and the results are listed in Table III below.

TABLE III

Tensile Properties of Natural Rubber Films Cured With
Both Sulfur and Peroxide But Without Sulfur Accelerators

| Test No. | PHR of Sulfur | PHR of Dicumyl Peroxide | 100% Modulus (PSI) | 300% Modulus (PSI) | 500% Modulus (PSI) | Ultimate Tensile Strength (PSI) | Ultimate Elongation (%) t | Toluene Swell (%) |
|---|---|---|---|---|---|---|---|---|
| 3.1 | 0.0 | 1.2 | 81 | 149 | 405 | 4051 | 881 | 89 |
| 3.2 | 0.2 | 1.2 | 80 | 136 | 322 | 4014 | 904 | 93 |
| 3.3 | 0.4 | 1.2 | 82 | 143 | 339 | 3956 | 924 | 92 |
| 3.4 | 0.6 | 1.2 | 79 | 137 | 333 | 3424 | 895 | 95 |
| 3.5 | 0.8 | 1.2 | 84 | 148 | 365 | 3737 | 909 | 92 |
| 3.6 | 1.0 | 1.2 | 82 | 146 | 345 | 3545 | 912 | 93 |

A difference between these results and the corresponding results obtained with cis-1,4-polyisoprene is that sulfur vulcanization appears to produce no improvement in tensile strength, although small improvements are seen in ultimate elongation (an increase) and 500% tensile modulus (a decrease). The sulfur also has a lesser effect on the toluene swell values in natural rubber latex than in the cis-1,4-polyisoprene latex.

EXAMPLE 4

Comparative

For comparison, this example presents test results on a series of latex formulations that were vulcanized with peroxide but not sulfur. Formulations both with and without a peroxide coagent were tested, as were different ratios of peroxide to coagent and different total amounts of peroxide and coagent.

The materials, compounding procedures, and test procedures were the same as those of the preceding examples, except that the peroxide coagent was Sartomer 521 (a difunctional methacrylate identical to Sartomer 231 but containing a scorch retarder), only 1 phr silica was used, and neither sulfur, zinc oxide, SBR rubber, surfactant, nor antioxidant were used. The test results are listed in Table IV.

The data in Table IV show that although the coagent was able to lower the 500% tensile modulus, it was not possible to simultaneously lower the modulus, increase ultimate tensile strength and increase ultimate elongation.

EXAMPLE 5

Comparative

For further comparison, this example presents test results on a further series of latex formulations that were vulcanized with peroxide but not sulfur. These formulations differed from those of Example 4 by containing additional reinforcing reagents in the form of 2 phr silica (rather than 1 phr as in Example 4) and the SBR rubber latex, plus the surfactant and the antioxidant of Example 1. As in Example 4, formulations both with and without the peroxide coagent (Sartomer 231) were tested, as were different ratios of peroxide to coagent and different total amounts of peroxide and coagent. Again, neither sulfur nor zinc oxide were included.

The materials, compounding procedures, and test procedures were the same as those of the preceding examples, and the test results are listed in Table V.

TABLE IV

Tensile Properties of Synthetic Polyisoprene
Films Cured With Peroxide Alone

| Test No. | Weight Ratio of Dicumyl Peroxide to SARET 521 | PHR of Combined Peroxide and SARET | 100% Modulus (PSI) | 300% Modulus (PSI) | 500% Modulus (PSI) | Ultimate Tensile Strength (PSI) | Ultimate Elongation (%) |
|---|---|---|---|---|---|---|---|
| 4.1 | 100/0 | 1.25 | 87 | 188 | 384 | 3435 | 751 |
| 4.2 | 90/10 | 1.25 | 70 | 159 | 315 | 2771 | 774 |
| 4.3 | 80/20 | 1.25 | 68 | 150 | 283 | 2827 | 798 |
| 4.4 | 70/30 | 1.25 | 66 | 138 | 258 | 2566 | 839 |
| 4.5 | 60/40 | 1.25 | 64 | 131 | 218 | 2742 | 884 |
| 4.6 | 80/20 | 1.5 | 88 | 186 | 385 | 3168 | 737 |
| 4.7 | 70/30 | 1.5 | 84 | 171 | 325 | 3182 | 796 |
| 4.8 | 35/65 | 1.5 | 63 | 107 | 164 | 3244 | 1062 |

TABLE V

Tensile Properties of Synthetic Polyisoprene Films Cured With Peroxide Alone Plus Reinforcing Agents

| Test No. | Weight Ratio of Dicumyl Peroxide to SARET 231 | PHR of Combined Peroxide and SARET | 100% Modulus (PSI) | 300% Modulus (PSI) | 500% Modulus (PSI) | Ultimate Tensile Strength (PSI) | Ultimate Elongation (%) |
|---|---|---|---|---|---|---|---|
| 5.1 | 100/0 | 1.2 | 100 | 251 | 618 | 3336 | 707 |
| 5.2 | 35/65 | 2.25 | 76 | 164 | 308 | 2665 | 864 |
| 5.3 | 35/65 | 2.5 | 79 | 173 | 331 | 3017 | 859 |
| 5.4 | 35/65 | 2.75 | 82 | 186 | 375 | 3051 | 809 |
| 5.5 | 35/65 | 3.0 | 87 | 202 | 421 | 2989 | 773 |
| 5.6 | 35/65 | 3.5 | 96 | 235 | 545 | 3091 | 710 |
| 5.7 | 35/65 | 3.75 | 100 | 248 | 649 | 2921 | 681 |
| 5.8 | 30/70 | 2.25 | 72 | 150 | 262 | 2690 | 1935 |
| 5.9 | 30/70 | 2.5 | 75 | 162 | 296 | 2743 | 886 |
| 5.10 | 30/70 | 2.75 | 80 | 178 | 351 | 2661 | 838 |
| 5.11 | 30/70 | 3.0 | 85 | 188 | 364 | 2762 | 826 |

Comparison of the data in Table V with that of Table IV shows that the inclusion of additional reinforcing agents fails to accomplish the objective of achieving all three improvements, i.e., reducing tensile modulus, increasing tensile strength, and increasing ultimate elongation.

The foregoing is offered primarily for purposes of illustration. It will be readily apparent to those skilled in the art that further variations and modifications can be made while still within the spirit and scope of the invention.

What is claimed is:

1. A method for forming a thin-walled rubber article, said method comprising:
    (a) forming an aqueous latex comprising vulcanizable rubber, a sulfur-containing vulcanizing agent, a crosslinking agent that forms carbon-carbon crosslinks, and water, said latex being devoid of vulcanization accelerators that contain secondary amine groups; and
    (b) forming said aqueous latex into said thin-walled rubber article by:
        (i) forming said aqueous latex into a film,
        (ii) evaporating water from said film, and
        (iii) subjecting said vulcanizable rubber to vulcanization conditions either before step (i), between steps (i) and (ii), after step (ii), or both before step (i) and after step (ii).

2. A method in accordance with claim 1 in which step (b) comprises forming said aqueous latex into a film, evaporating water from said film, and subjecting said film to vulcanization conditions after evaporating water from said film.

3. A method in accordance with claim 1 in which step (b) comprises subjecting said aqueous latex to vulcanization conditions, forming said aqueous latex thus vulcanized into a film, and evaporating water from said film thus formed.

4. A method in accordance with claim 1 in which step (b) comprises subjecting said aqueous latex to vulcanization conditions, forming said aqueous latex thus vulcanized into a film, evaporating water from said film thus formed, and subjecting said film to vulcanization conditions after evaporating water from said film.

5. A method in accordance with claim 1 in which said film of step (b)(i) has a thickness of about 0.02 inch or less.

6. A method in accordance with claim 1 in which said film of step (b)(i) has a thickness of from about 0.001 inch to about 0.02 inch.

7. A method in accordance with claim 1 in which said aqueous latex is devoid of all reaction species that contain secondary amine groups.

8. A method in accordance with claim 1 in which said aqueous latex is devoid of sulfur vulcanization accelerators.

9. A method in accordance with claim 1 in which step (b)(i) comprises dipping in said latex a forming member having an outer surface with a contour complementary to that of said article and withdrawing said forming member from said latex in such a manner as to leave a film of said latex over said surface.

10. A method in accordance with claim 1 in which said vulcanizable rubber is protein-free synthetic cis-1,4-polyisoprene.

11. A method in accordance with claim 1 in which said sulfur-containing vulcanizing agent is elemental sulfur.

12. A method in accordance with claim 1 in which said vulcanizing agent that forms carbon-carbon crosslinks is an organic peroxide.

13. A method in accordance with claim 12 in which said organic peroxide is a member selected from the group consisting of diacyl peroxides, dialkyl peroxides, peroxyketals, monoperoxy carbonates, acetyl alkylsulfonyl peroxides, dialkyl peroxydicarbonates, tert-alkyl hydroperoxides, peroxy esters, and acetyl alkylsulfonylperoxides.

14. A method in accordance with claim 12 in which said organic peroxide is a member selected from the group consisting of dicumyl peroxide, di(2-t-butyl peroxy isopropyl) benzene, 2,5-dimethyl-2,5-di(t-butyl-peroxy)hexane, dibenzoyl peroxide, 2,4-dichlorobenzyl peroxide, and n-butyl-4,4-bis(t-butylperoxy)valerate.

15. A method in accordance with claim 12 in which said organic peroxide is dicumyl peroxide.

16. A method in accordance with claim 12 in which said organic peroxide is di(2-t-butyl peroxy isopropyl) benzene.

17. A method in accordance with claim 1 in which said sulfur-containing vulcanizing agent is elemental sulfur at a maximum concentration of about 10 phr, and said vulcanizing agent that forms carbon-carbon crosslinks is dicumyl peroxide at a maximum concentration of about 3 phr.

18. A method in accordance with claim 1 in which said sulfur-containing vulcanizing agent is elemental sulfur at about 0.01 phr to about 6 phr, and said vulcanizing agent that forms carbon-carbon crosslinks is dicumyl peroxide at from about 0.05 phr to about 3 phr.

19. A method in accordance with claim 1 in which said sulfur-containing vulcanizing agent is elemental sulfur at about 0.1 phr to about 0.6 phr, and said vulcanizing agent that forms carbon-carbon crosslinks is dicumyl peroxide at from about 0.1 phr to about 2 phr.

20. A method in accordance with claim 1 in which said vulcanization conditions include avoidance of contact of said vulcanizable rubber with molecular oxygen.

21. A method in accordance with claim 2 further comprising forming an oxygen-impermeable barrier over said film before subjecting said film to vulcanization conditions.

22. A method in accordance with claim 21 in which said oxygen-impermeable barrier is a polyvinyl alcohol coating.

23. A method in accordance with claim 2 in which said vulcanization conditions comprise immersing said film in a chemically inert liquid bath at a temperature and for a sufficient period of time to effect vulcanization.

24. A method in accordance with claim 4 in which said vulcanization conditions comprise immersing said film in a chemically inert liquid bath at a temperature and for a sufficient period of time to effect vulcanization.

25. A method in accordance with claim 1 in which step (a) comprises combining an aqueous dispersion of vulcanizable rubber, an aqueous dispersion of a sulfur-containing vulcanizing agent that does not contain a secondary amine group, and an aqueous dispersion of a vulcanizing agent that forms carbon-carbon cross-links.

26. A method in accordance with claim 1 in which step (a) comprises combining an aqueous dispersion of vulcanizable rubber, an aqueous dispersion of elemental sulfur, and an aqueous dispersion of an organic peroxide vulcanizing agent.

27. A method in accordance with claim 1 in which step (b)(i) comprises dipping a forming member first in a coagulant solution to leave a coagulant solution film over said forming member, and dipping said forming member with said coagulant solution film in said latex to leave a film of said latex over said forming member, said forming member having an outer surface with a contour complementary to that of said article.

28. A method in accordance with claim 1 in which said aqueous latex further comprises a peroxide coagent comprised of a difunctional acrylate ester.

29. A method in accordance with claim 1 in which said aqueous latex further comprises a silica reinforcing agent.

30. A method in accordance with claim 1 in which said aqueous latex further comprises a stabilizing amount of an antioxidant.

31. A method in accordance with claim 30 in which said antioxidant is a hindered phenolic compound.

32. A method in accordance with claim 30 in which said hindered phenolic compound is a member selected from the group consisting of 4-{[4,6-bis(octylthio)-s-triazin-2-yl]amino}-2,6-di-t-butylphenol, 2,4-bis[(octylthio)methyl-o-cresol, and polymerized 1,2-dihydro-2,2,4-trimethylquinoline.

33. A method in accordance with claim 1 in which said aqueous latex further comprises carboxylated styrene butadiene rubber having a styrene content of at least 50% styrene.

34. A method in accordance with claim 1 in which said sulfur-containing vulcanizing agent is elemental sulfur, and said aqueous latex further comprises zinc oxide in an amount ranging from about 0.03 phr to about 1 phr.

\* \* \* \* \*